(12) United States Patent
Maack et al.

(10) Patent No.: US 10,813,618 B2
(45) Date of Patent: Oct. 27, 2020

(54) TEST OBJECT FOR CALIBRATION OF AN X-RAY IMAGING DEVICE

(71) Applicant: KONINKLIJKE PHILIPS N.V., Eindhoven (NL)

(72) Inventors: Hanns-Ingo Maack, Norderstedt (DE); Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/307,659

(22) PCT Filed: Jun. 8, 2017

(86) PCT No.: PCT/EP2017/063968
§ 371 (c)(1),
(2) Date: Dec. 6, 2018

(87) PCT Pub. No.: WO2017/211955
PCT Pub. Date: Dec. 14, 2017

(65) Prior Publication Data
US 2019/0307414 A1 Oct. 10, 2019

(30) Foreign Application Priority Data
Jun. 8, 2016 (EP) .................................. 16173549

(51) Int. Cl.
*A61B 6/00* (2006.01)
(52) U.S. Cl.
CPC ............ *A61B 6/583* (2013.01); *A61B 6/4291* (2013.01); *A61B 6/587* (2013.01)
(58) Field of Classification Search
None
See application file for complete search history.

(56) References Cited

U.S. PATENT DOCUMENTS

| 2001/0002925 A1* | 6/2001 | Siffert .................. A61B 6/482 378/56 |
| 2003/0072417 A1 | 4/2003 | Kaufhold |

(Continued)

FOREIGN PATENT DOCUMENTS

| JP | S63247870 A | 10/1988 |
| WO | WO2014206841 A1 | 12/2014 |

(Continued)

OTHER PUBLICATIONS

Pfeiffer, R. et al., "Hard-X-Ray Dark-Field Imaging Using a Grating Interferometer", Nature Materials, vol. 7, No. 2, pp. 134-137, Feb. 2008.

(Continued)

*Primary Examiner* — Hoon K Song
(74) *Attorney, Agent, or Firm* — Larry Liberchuk

(57) ABSTRACT

A calibration method and corresponding object for calibrating an X-ray imaging system with respect to dark field imaging is disclosed. The calibration object (1) generically comprises a plurality of sections (10, 20), wherein at least a part of the sections comprises two different materials, respectively. One material (101, 201) in a corresponding section leads to attenuation of passing X-ray beams and the other material (102, 202) is a dark field active material leading to small-angle scattering signals of incident X-rays. The ratio of the two materials in one section varies from section to section. The calibration object can be used to calibrate an X-ray imaging system with respect to a non-linear behavior of the dark field visibility.

12 Claims, 5 Drawing Sheets

(56) References Cited

U.S. PATENT DOCUMENTS

2004/0028181 A1* 2/2004 Charles, Jr. ............ A61B 6/032
378/92
2015/0110247 A1 4/2015 Baturin

FOREIGN PATENT DOCUMENTS

| WO | WO2015067511 A1 | | 5/2015 |
|----|-----------------|---|--------|
| WO | WO2015180977    | * | 12/2015 |
| WO | WO2015180977 A1 |   | 12/2015 |

OTHER PUBLICATIONS

Bech, M. et al., "Quantitative X-Ray Dark-Field Computed Tomography", Physics in Medicine and Biology, vol. 55, No. 18, pp. 5529-5539, Sep. 2010.

* cited by examiner

4

5

1

TEST OBJECT FOR CALIBRATION OF AN X-RAY IMAGING DEVICE

FIELD OF THE INVENTION

The invention relates to a calibration object for an X-ray imaging device, to a method for calibrating an X-ray imaging device, a computer program and a computer readable medium.

BACKGROUND OF THE INVENTION

X-ray imaging has recently taken developments in a variety of contrast mechanisms, including transmission imaging, phase contrast imaging, and dark field imaging. Background related to the latter dark field imaging contrast mechanism can, for instance, be found in Pfeiffer et al., "Hard-X-ray dark-field imaging using a grating interferometer", Nature Publishing Group, doi: 10.1038/nmat2096.

Dark field images, or more generally scattering based images, are based on the local scattering power of a sample and are formed from small-angle diffraction intensities scattered by the sample instead of the attenuated intensities as in case of transmission imaging.

In conventional transmission X-ray imaging, beam hardening leads to artifacts and must be corrected in order to provide accurate images appropriate for diagnostic or other image based reasoning tasks.

Similar artifacts are present in dark field imaging. In the past, a correction similar to a beam hardening correction has been applied in dark field imaging.

SUMMARY OF THE INVENTION

There may therefore be a need for a different method and a related object for calibration of X-ray imaging systems for dark field imaging, or more generally scattering based imaging with X-rays.

The object of the present invention is solved by the subject matter of the independent claims where further embodiments are incorporated in the dependent claims.

According to a first aspect of the invention a calibration object for calibrating an X-ray imaging device used for dark field imaging is provided. The calibration object comprises a plurality of sections. A first section out of the plurality of sections comprises a first, regular material (where the dominant interaction with the X-rays is attenuation) and a second, dark field active material, preferably a material that attenuates the X-rays only very little and leads to small-angle scattering. Similarly, a second section out of the plurality of sections comprises a first, regular material and a second, dark field active material. Thereby, the ratio of the first, regular material to the second, dark field active material in the first section differs from the ratio of the first, regular material to the second, dark field active material in the second section.

The calibration object of the present invention can be beneficially used during the calibration method of the present invention as will be further elaborated on hereinafter. In particular, the data acquired from exposing such a calibration object, e.g. one of the calibration objects depicted in FIGS. 1 to 7, to X-ray beams can be used to linearize the performance of a dark field imaging system and hence for calibration of the X-ray imaging system as regards dark field images.

In other words a test phantom, i.e., the calibration object, is disclosed herein to calibrate systems of dark field imaging. The resulting data can be used to linearize the performance of the dark field image. Thus, using this calibration object, i.e. a test object, as described here, the dark field imaging system can be calibrated to achieve a better linear relation of object height and the logarithm of the dark field signal D. The more linear data will advantageously allow computer aided decision based on quantitative imaging.

The calibration object of the present invention may in general be single structural element but alternatively may also consist of two or more structural elements which can be mechanically arranged together to finally build the calibration object used during the calibration of the X-ray imaging device. This will be explained hereinafter in more detail based on exemplary embodiments.

The calibration object may have the shape of a rectangular solid, a pyramid, a step pyramid or may have any other three-dimensional geometrical shape, as will become apparent from the following disclosure. A section of the calibration object may comprise a part of the volume of the calibration object. For instance, the aforementioned part of the volume of the calibration object may be given by the volume extending between a part of the bottom surface and a part of the top surface of the object. In the latter case, the volume might be characterized in terms of a base or cross sectional area, for instance associated with the aforementioned part of the bottom surface, and a height of the calibration object. Here, a height of the calibration object refers to a distance between the bottom surface and the top surface of the calibration object.

A difference in the aforementioned ratios may generally arise due to different heights of the parts filled by a regular material or a dark field active material in corresponding sections.

According to one embodiment of the invention, a regular material comprises one of the materials PMMA (Polymethylmethacrylat), POM (Polyoxymethylen), PE (Polyethylen), Aluminum, or a combination of any of the aforementioned materials. A regular material attenuates a traversing X-ray to different signal levels, depending on the material and the thickness of the material traversed by the X-ray. It is supposed to create no or only very little dark field signal.

According to one embodiment of the invention, a dark field active material comprises one of the materials tissue, (hollow) glass spheres, (hollow) glass spheres in resin, foam, glass fibers, or any combination of the aforementioned materials. A dark field active material in general contains structures, which are in the range from some 100 nm to some 10 μm. These structures lead to small-angle scattering signals of incident X-rays, which form the basis of the small-angle diffraction intensities scattered by a sample and recorded for subsequent analysis in dark field imaging. In an embodiment related, for instance, to clinical applications, the dark field active material has a similar shape as the dark-field active tissue, which will be analyzed with the dark field imaging system after its calibration. For instance, if the system will be used after calibration for lung imaging, the preferred material is a closed cell foam with cell size in the order of 50 to 300 μm and wall thickness in the order of few μm or hollow spheres of corresponding size. If the system will be used after calibration for bone imaging, the preferred material is an open cell foam, where the foam ligaments have similar size as trabecula (some ten to a few 100 μm).

According to one embodiment of the invention, the calibration object comprises in the first and in the second section a third material. The third material can be a regular material or a dark field active material. The third material may differ from the first, regular material and the second, dark field active material comprised in the first and second section. For instance, the calibration object might be used in order to calibrate a dark field imaging system for later use in lung imaging. For this clinical application, the first, regular material might be chosen to comprise POM as a surrogate for soft tissue and the second, dark field active material could be chosen to be a closed cell foam as a lung-equivalent material. As a third material comprised in the first and the second section of the calibration object, Aluminum could be used as surrogate for bones.

According to one embodiment of the invention, similar to the embodiment shown in FIG. 3, a section of the calibration object can comprise a first and a second subsection. In this case, the first subsection comprises a part of the volume of the section and can be attributed a cross sectional area and a first height. The second subsection comprises the remaining part of the volume of the section and has a second height. Accordingly, the first subsection and the second subsection of a section do not overlap, that is, they are disjoint or, in other words, are not sharing a common volume. The first subsection may comprise the regular material, whereas the second subsection comprises the dark field active material. Several sections of the calibration object may comprise a first and a second subsection with the aforementioned properties. In this case, the height of the first subsection may vary from section to section, respectively. Accordingly, also the height of the second subsection may vary from section to section. The first and second subsections of a corresponding section are arranged such that a beam of X-rays traversing a section may successively traverse the first and the second subsection. Further aspects of this embodiment will be elucidated in the context of the embodiment shown in FIG. 3. According to the aforementioned embodiment, the height, or, in other words, the thickness, of a section is given by the sum of the heights of its subsections.

The height of a section can be chosen such that it corresponds to a height or thickness of a sample to be examined/analyzed with the dark field imaging system after calibration.

According to one embodiment of the invention, the calibration object comprises a first and a second step wedge. The first step wedge comprises a regular material and the second step wedge comprises a dark field active material. Both step wedges may have at least three steps, yet the number of steps per step wedge may be e.g. of the order of ten, twenty or larger. Moreover, the number of steps of the first step wedge may be or may not be equal to the number of steps of the second step wedge. The arrangement of the step wedges may be such, that the second step wedge is arranged over the first step wedge. The steps of the second step wedge may extend lengthwise in a plane parallel to the longitudinal extension of the steps of the first step wedge. However, the orientation of the longitudinal extension of the steps of the second step wedge can also be rotated by 90° with respect to the longitudinal extension of the steps of the first step wedge.

In the aforementioned embodiment with the arrangement of two step wedges, a section extends along an axis perpendicular to the longitudinal extensions of the first and the second step wedges. Accordingly, in this embodiment, a section of the calibration object may exhibit a first subsection formed by a part of a step of the first step wedge. A corresponding second subsection of the section may be formed by a part of a step of the second step wedge. This arrangement ensures that a section comprises two not overlapping subsections, one with a regular material and the other with a dark field active material.

According to an embodiment of the invention, the calibration object comprises a step wedge and a fluid. The step wedge comprises a dark field active material and is submerged into the fluid, which comprises a regular material. The fluid may be water. According to an embodiment of the invention, the height of the first section may equal the height of the second section of the calibration object. In this way, a constant patient height, or height—or thickness—of a sample to be examined can be simulated.

According to a second aspect of the invention, there is provided a method for calibrating an X-ray imaging device for acquisition of dark field imaging data. The method comprises the following steps:

A calibration object according to an embodiment of the invention is positioned in the beam path of X-ray beams of an X-ray imaging device. The calibration object is exposed to X-rays such, that an X-ray beam may traverse a specific section of the calibration object. That is, the calibration object should be positioned relative to the beam direction in such a way, that a specific X-ray passes through a section and preferably not through a plurality of sections of the calibration object. By exposing the calibration object in the aforementioned manner to an X-ray source, a dark field test image is acquired from the calibration object. Subsequently, pairs of values $\log(T_i)$ and $\log(D_i)$ are obtained from the dark field test image for each section i of the calibration object. Thereby, $T_i=I_i/I_{i0}$ denotes the ratio of an actual mean X-ray intensity $I_i$ to the mean X-ray intensity $I_{i0}$ in absence of the calibration object, corresponding to the ith section of the calibration object. For instance, a mean X-ray intensity is derived from acquired intensity data with a fringe pattern, which may result from the use of a grating based interferometer, by taking the mean over all phases of the fringe pattern. Similarly, $D_i=V_i/V_{i0}$ denotes the ratio of an actual visibility $V_i$ to the visibility $V_{i0}$ in absence of the calibration object, again corresponding to the ith section of the calibration object.

In a next step the values $\log(T_i)$ and $\log(D_i)$ for each section i are compared with expected design parameters, for instance the thickness or height, of the calibration object. Based on the comparison, a function, which maps the measured log(T) and log(D) data to the thicknesses of the regular material and the dark field active material, respectively, is constructed. A more detailed exemplary description of the construction of the function is provided later on with reference to FIG. 7.

According to one embodiment of the invention, a two-dimensional look-up table is constructed from the function in a further method step.

According to one embodiment of the invention, the function and/or the two-dimensional look-up table are used to correct clinical images based on dark field imaging.

According to one embodiment of the invention, several pairs of values $\log(T_i)$ and $\log(D_i)$ are obtained for each section i of the calibration object, corresponding to different X-ray energies. Such situation arises when an X-ray energy resolving detector is used for obtaining the values of log(T) and log(D). For instance, two pairs of values log(T) and log(D) corresponding to two different X-ray energies may be obtained using an X-ray energy resolving detector. Having this additional information of $\log(T_i)$ and $\log(D_i)$ at different energies for each section, it is possible to generate a function that maps the measured log(T) and log(D) data to the thicknesses of the regular material, the dark field active material, and a third material, respectively.

According to one embodiment of the invention, a three-dimensional look-up table is constructed from the function in a further method step.

It should be noted that the aspects of the invention related to the method for calibration of an X-ray device similarly apply to the computer program and the computer readable medium.

BRIEF DESCRIPTION OF THE DRAWINGS

Exemplary embodiments of the invention will now be described with reference to the following drawings therein.

DETAILED DESCRIPTION OF EMBODIMENTS

Figure 1:
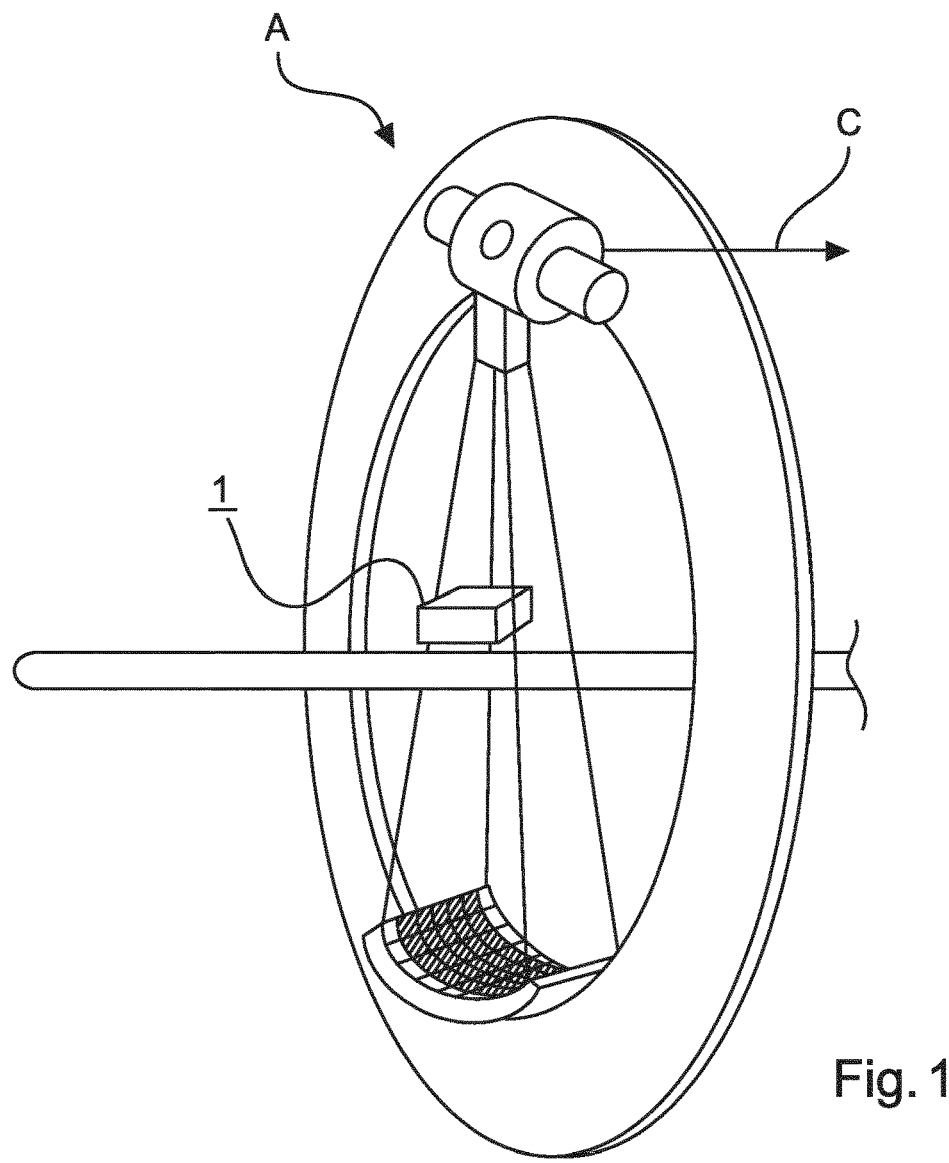
FIG. 1 shows an imaging arrangement with a calibration object.

With reference to FIG. 1, there is shown an X-ray imaging system A with a calibration object 1 for calibrating the X-ray imaging system according to one embodiment of the present invention. The X-ray system comprises an X-ray source and an X-ray detector for detecting the intensity of X-ray beams. The calibration object 1 is arranged in the beam path of the X-rays between the X-ray source and the X-ray detector. Furthermore, the X-ray imaging system comprises a computing system C for further processing of the X-ray related data recorded with the X-ray detector. In such a way the X-ray imaging device can be calibrated by using the calibration method explain herein in detail, e.g. in the context of FIG. 7.

Figure 2:
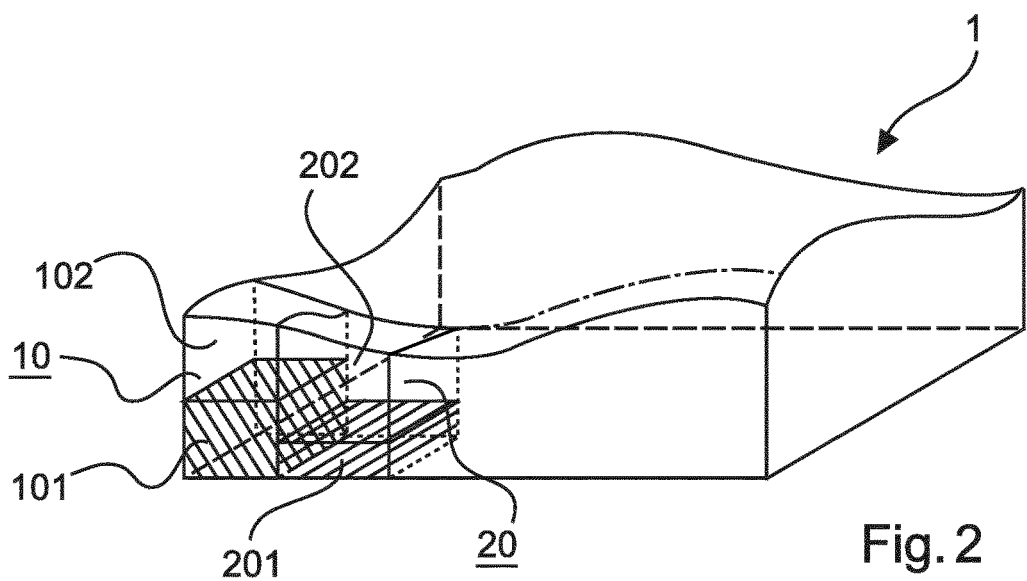
FIG. 2 shows a schematic representation of a calibration object according to an exemplary embodiment of the present invention.

FIG. 2 illustrates schematically a calibration object 1 according to one embodiment of the present invention. The calibration object 1 shown has a generally cuboid shape. However, the upper surface of the exemplary calibration object 1 in FIG. 2 is not plane but curved. Generally, the 3-dimensional shape of the calibration object is not fixed but can take any form providing a 3-dimensional volume for passage of X-ray beams. The calibration object can be divided into a plurality of sections. Two such sections, a first section 10 and a second section 20, are exemplarily shown in FIG. 2. Each section comprises a volume between the upper and the lower surface of the calibration object 1, such that an X-ray beam originating from an X-ray source arranged above the calibration object may pass from top to bottom through a given section. The first section 10 comprises a first, regular material 101 and a second, dark field active material 102, filling a certain part of the total volume of the first section, respectively. In particular, as shown in FIG. 2, the part of the volume of the first section 10 filled with the first regular material 101 differs from the corresponding part of the volume with the second, dark field active material 102, such that the sum or spatial combination of the two respective parts makes up the first section 10. In a similar manner, the second section 20 comprises a first regular material 201 and a second, dark field active material 202, wherein each of the two material 201 and 202 may or may not be identical to the respective materials in the first section 10. The arrangement of the regular material 201 and the dark field active material 202 in the second section 20 is analogous to the corresponding arrangement of materials 101 and 102 in the first section 10. In case of FIG. 2, the regular material 101 in the first section 10 fills a volume of size comparable to the volume filled by the dark field active material 102. Contrarily, the volume of the second section 20 filled by the regular material 201 is considerably smaller than the volume filled by the dark field active material 202. Accordingly, the ratio of the volumes filled by the regular material 101 and the dark field active material 102 in the first section 10 differs from the corresponding ratio in case of the regular material 201 and the dark field active material 202 in section 20.

A difference in the aforementioned ratios may generally arise due to different heights of the parts filled by a regular material or a dark field active material in corresponding sections.

Figure 3:
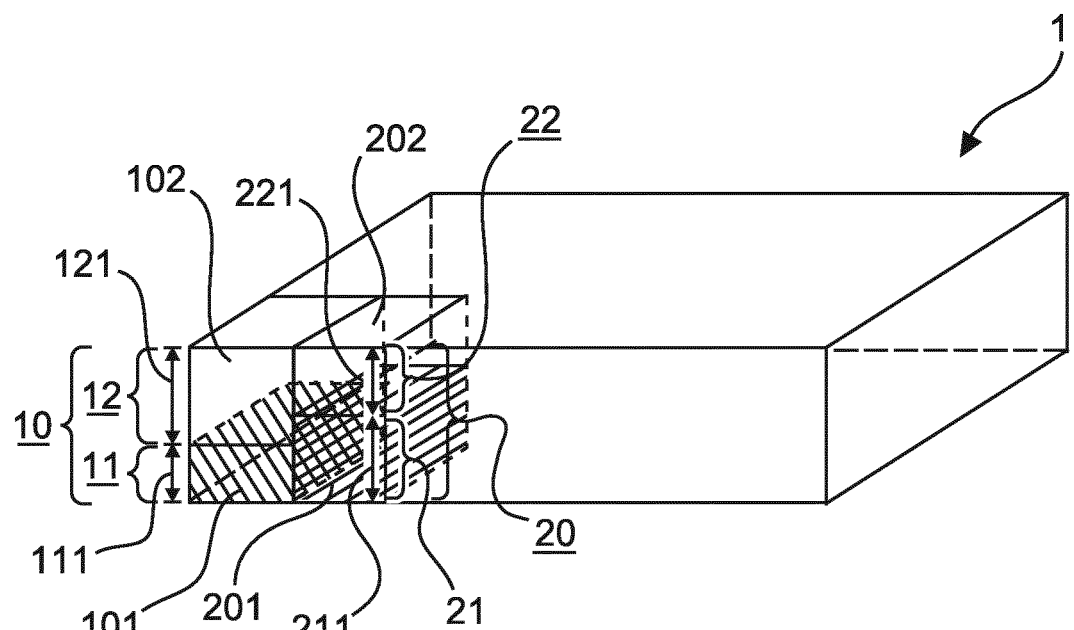
FIG. 3 shows another schematic representation of a calibration object according to an exemplary embodiment of the present invention.

With reference to FIG. 3, a calibration object 1 according to another exemplary embodiment is shown with an overall cuboid shape. The calibration object 1 comprises a plurality of sections out of which two, a first section 10 and a second section 20, are shown in FIG. 3. Both sections 10 and 20 have the same cross sectional area as well as the same overall height, whereas the height is measured from the bottom to the top of the calibration object 1 in the arrangement as shown in FIG. 3. The height of the first section 10 can be described as the sum of heights 111 and 121, corresponding to a first subsection 11 and a second subsection 12 of first section 10. Thereby, the first subsection 11 comprises a regular material 101 and the second subsection 12 comprises a dark field active material 102. Similarly, the overall height of the second section 20 is given by a sum of heights 211 and 221 corresponding to a first and second subsection 21 and 22 of second section 20, respectively. The first subsection 21 comprises a regular material 201 and the second subsection 22 comprises a dark field active material 202. As the heights 111 and 211 comprising a regular material in the first and second section differ, the ratio of the volumes comprising the regular material and the dark field active material in a given section is different in case of sections 10 and 20.

Figures 4A, 4B:
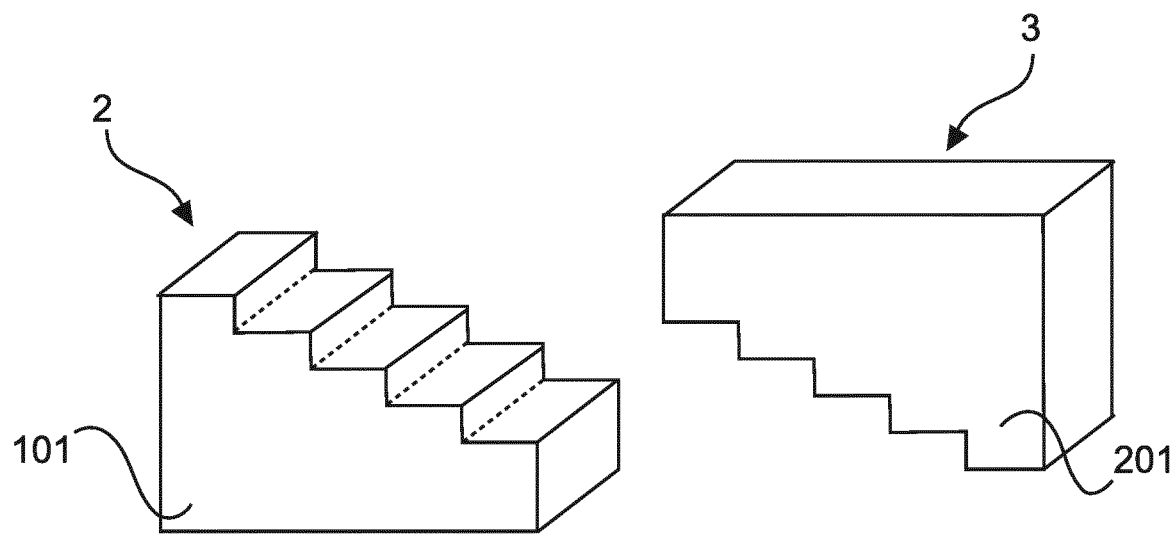
FIG. 4A shows a schematic representation of a first step wedge of a calibration object of an exemplary embodiment of the present invention.
FIG. 4B shows a schematic representation of a second step wedge of a calibration object of an exemplary embodiment of the present invention.

With reference to FIG. 4A and FIG. 4B, two step wedges 2 and 3 are shown, which can be used to construct a calibration object according to an embodiment. The step wedge 2 may comprise a regular material 101 and the step wedge 3 may comprise a dark field active material 201. The two step wedges 2 and 3 may be moved in a position, in which the steps of the step wedge 3 are positioned upon the steps of step wedge 2, or vice versa. In case that the number of steps per step wedge is the same, as shown in FIG. 3, a calibration object can be obtained, which comprises a plurality of sections—five sections in case of the present example—wherein each of the sections is given by the sum of a step from step wedge 2 and a step from step wedge 3. The number of five steps per step wedge is exemplary and may vary in different embodiments. A minimal number of steps per step wedge may be three, but there may be embodiments with e.g. an order of ten or twenty steps per step wedge, but also other number of steps are of course part of the present invention. The height, i.e. the thickness, of the highest step may be such that it represents the highest thickness of a sample to be examined or analyzed with the dark field imaging system after calibration. For instance, if the dark field imaging system will be used for lung imaging after calibration, the maximal height—or in other words the highest thickness—of a step in one of the step wedges may correspond to the (actual, average or expected) thickness of a human or animal thorax to be examined.

Figure 5A:
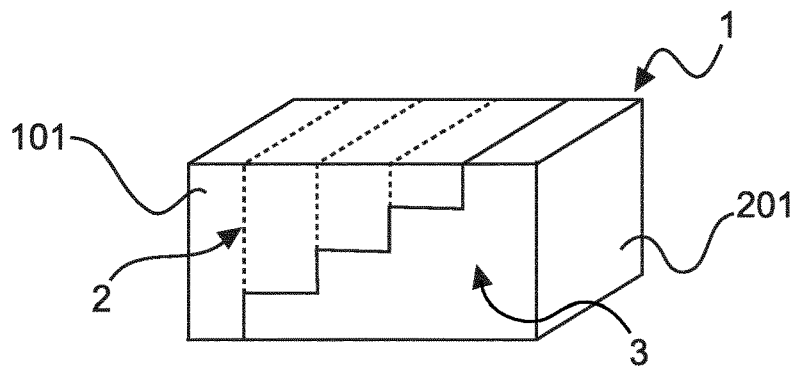
FIG. 5A schematically shows a calibration object comprising a first and a second step wedge according to an exemplary embodiment of the present invention.

With reference to FIG. 5A, a schematic illustration of a calibration object 1 according to one exemplary embodiment obtained from two step wedges 2 and 3 is shown. It is thus understood by the skilled reader that both components 2 and 3 are mechanically combinable to finally build the calibration object and is thus a two component embodiment. Embodiments comprising more than two components, e.g. three, four or more components, are to be understood to be part of the present invention. Step wedge 2 comprises a regular material 101 and step wedge 3 comprises a dark field active material 201. Each of the two step wedges 2 and 3 in FIG. 5A comprises four steps. The resulting calibration object comprises five sections in total, wherein the leftmost section in FIG. 5A contains the regular material 101 and the rightmost section contains the dark field active material 201. The three remaining sections comprise both the regular material and the dark field active material, wherein the ratio of the volumes taken by the two materials varies from section to section.

Figure 5B:
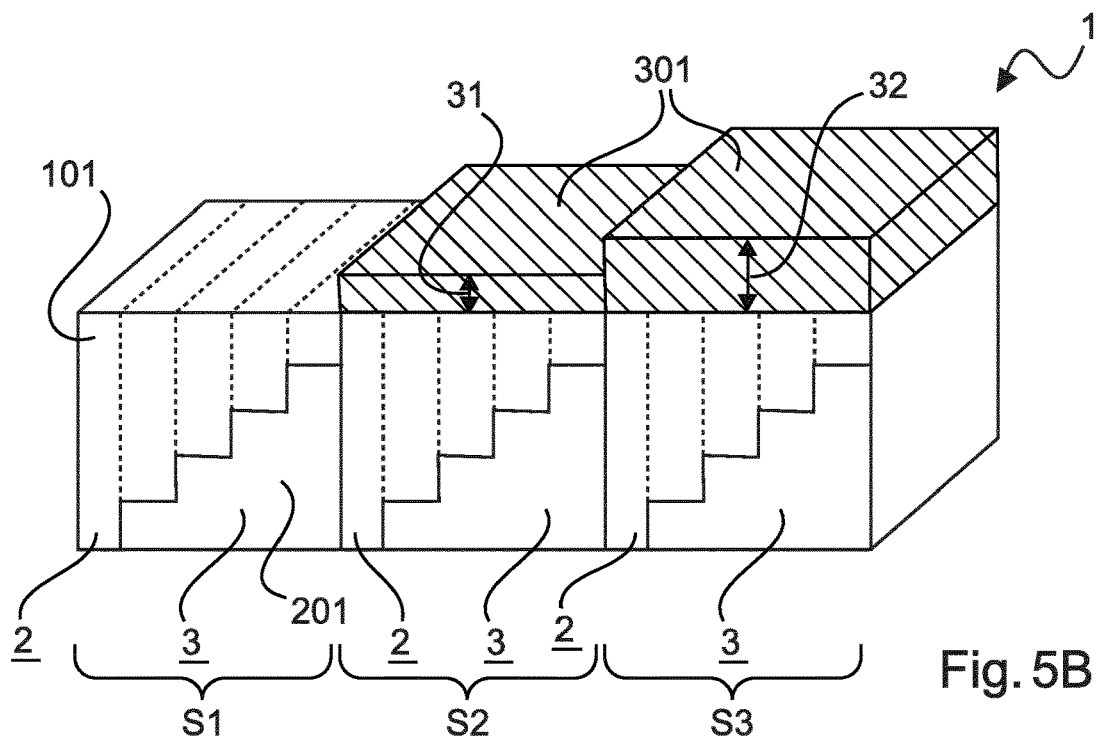
FIG. 5B schematically shows a calibration object comprising a third material according to an exemplary embodiment of the invention.

With reference to FIG. 5B, a schematic representation of a calibration object 1 with a third material according to one embodiment of the invention is shown. The calibration object 1 can, for instance, be obtained by assembling three calibration objects as shown in FIG. 5A and additionally arranging sheets of a third material over two of the latter three calibration objects known from FIG. 5A. In particular, the calibration object 1 in FIG. 5B can be divided into three subunits, S1, S2, S3, each of the subunits comprising a calibration object as shown in FIG. 5A. On top of the calibration objects as known from FIG. 5A, a sheet of a third material 301 is arranged in the second subunit S2 and the third subunit S3. Thereby, the sheet of the third material 301 in subunit S2 has a height, or thickness, 31 which is smaller than the height, or thickness, 32 of the sheet of the third material 301 in the third subunit. The third material 301 can be a regular material different from the regular material 101. A calibration object 1 as shown in FIG. 5B can be used for calibration of X-ray imaging systems providing improved precision in diagnostics for situations where there are more than two regular materials contained in a region of interest in a patient/sample/specimen. For instance, referring to the application of lung imaging, the regular material 101 in the calibration object 1 of FIG. 5B can be chosen to be POM having similar properties as soft tissue and the dark field active material 201 can be chosen to be a closed cell foam as a lung-equivalent material. The third material 301 could then be chosen as Aluminum as a surrogate for bones. It is understood by the skilled person that the third material 301 could also be chosen as a dark field active material differing from the dark field active material 201 in FIG. 5B.

Figure 5C:
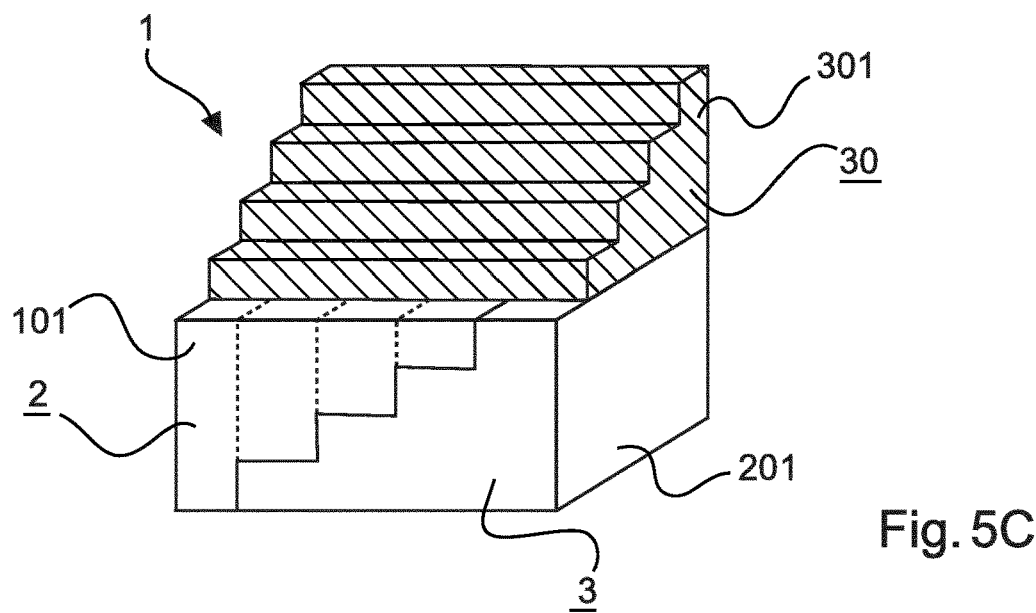
FIG. 5C schematically shows another calibration object comprising a third material according to an exemplary embodiment of the invention.

FIG. 5C schematically shows another calibration object 1 comprising a regular material 101, a dark field active material 201 and a third material 301. The calibration object 1 in FIG. 5C can be assembled by arranging a step wedge 30 of a third material 301 on top of the combination of two step wedges 2 and 3 as known from FIG. 5A. Thereby, the step wedge 2 comprises a regular material 101, the step wedge 3 comprises a dark field active material 201 and the third step wedge 30 comprises a third material 301, which can be a regular or a dark field active material. The calibration object in FIG. 5C can be used for calibration purposes as described in context of FIG. 5B.

Figure 6A:
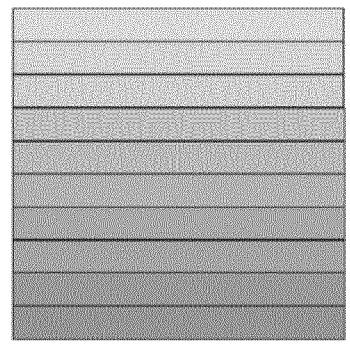
FIG. 6A schematically shows a top view of a first step wedge according to an exemplary embodiment of the present invention.
Figure 6B:
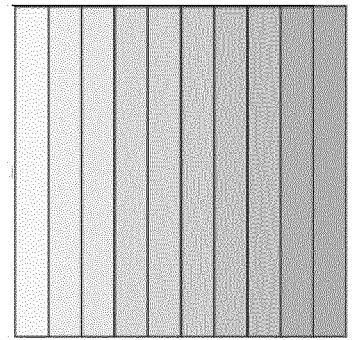
FIG. 6B schematically shows a top view of a second step wedge according to an exemplary embodiment of the present invention.
Figure 6C:
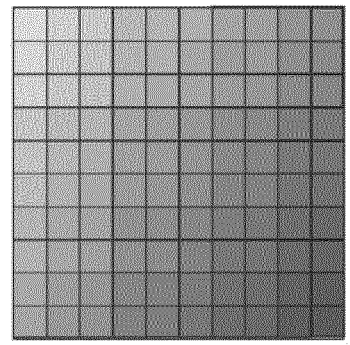
FIG. 6C shows a schematic representation of the combination of the first and second step wedges from FIGS. 6A and 6B.

With reference to FIG. 6C a schematic top view of a calibration object 1 according to one embodiment is shown. FIGS. 6A and 6B show schematic top views of a step wedge 4 comprising a regular material and a step wedge 5 comprising a dark field active material, respectively, which can be arranged on top of each other in order to obtain calibration object 1 in FIG. 6C. The different gray values of the horizontal bars in FIG. 6A indicate different heights of the steps of step wedge 4, which is seen from above in FIG. 6A. Similarly, the vertical bars in FIG. 6B depict the steps of step wedge 5 seen from above, and the different gray levels indicate the differing heights of the steps. As compared to the alignment of the steps of step wedge 4, the alignment of the steps of step wedge 5 is rotated by 90° with respect to an axis parallel to the line of sight in FIGS. 6A and 6B. Keeping the alignment of the steps as in FIGS. 6A and 6B and moving step wedge 5 over step wedge 4, a calibration object 1 is obtained. As each of the depicted step wedges 4 and 5 in FIGS. 6A and 6B comprises 10 steps, calibration object 1 can be constructed as to comprise hundred different sections, each section having a subsection build from a part of a step from step wedge 4 and another subsection built from a part of a step from step wedge 5. Accordingly, when exposing calibration object 1 to an X-ray beam, hundred different combinations of materials can be exposed to an X-ray beam, and corresponding dark field imaging data acquired during exposure can subsequently be analyzed.

In other words the embodiment of the calibration object shown in FIGS. 6A-6C is a test phantom which can be used to calibrate systems of Dark Field Imaging. It consists of two step wedges with different materials. One is of regular material such as PMMA, POM, or PE and attenuates the X-ray to different signal levels. The second new wedge is made of a dark field active material that contains structures of the order of some micrometers. Examples for this are fabric tissue of glass spheres. Experiments have been made with hollow glass spheres in a resin. If both step wedges have 10 steps, one can arrange them over each other with one being 90° rotated such as 100 different combination of material can be exposed.

Figure 7:
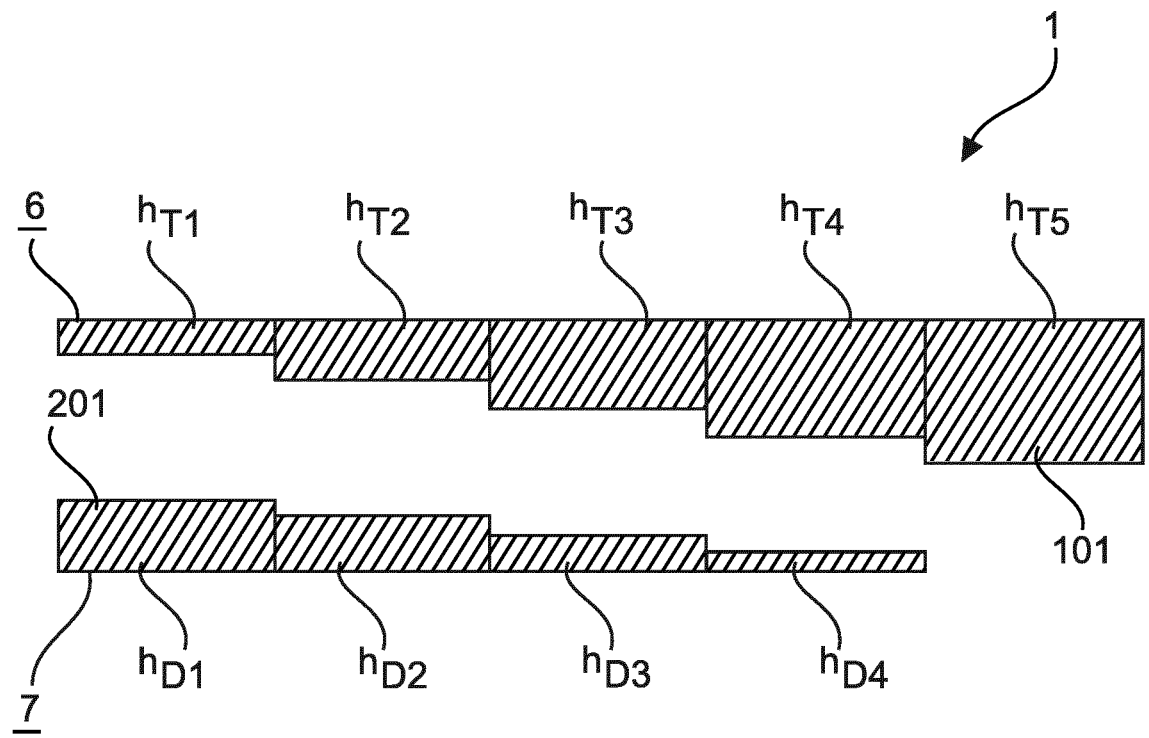
FIG. 7 schematically shows a side view of one row of a calibration object according to an exemplary embodiment of the present invention.

FIG. 7 schematically shows a side view of one row of a calibration object 1 according to an exemplary embodiment.

The calibration object 1 comprises two step wedges, a first step wedge 6 and a second step wedge 7. The first step wedge 6 comprises a regular material. It is constructed from several steps. In FIG. 7, five such steps are shown with different heights $h_{Ti}$. The second step wedge 7 in FIG. 7 comprises a dark field active material and is constructed from several steps. Four steps with different height $h_{Di}$ are shown exemplarily in FIG. 7. The first and the second step wedge can be arranged on top of each other, resulting in a calibration object build from two structural elements—the first and the second step wedge. The heights $h_{Ti}$ and $h_{Di}$ are selected such that their sum $h_{Ti}+h_{Di}$ correspond to the same patient/sample/specimen height at least for all sections in one row of the calibration object. Thereby, a section of the calibration object comprises a step with height $h_{Ti}$ from the first step 6 wedge and a step with height $h_{Di}$ from the second step wedge 7. In this way it is possible to simulate a height—or thickness—of a patient or other sample to be examined or analyzed with the dark field imaging system after its calibration. With respect to clinical applications, the regular material comprised in the first step wedge 7 could be chosen to behave exactly as soft tissue and the dark field active material could be chosen to behave exactly like lung tissue. In this case, the sum $h_{Ti}+h_{Di}$, should be constant in one row. If the regular material comprised in the first step wedge 6 is however more dense than soft tissue, for instance POM attenuating X-rays 1.3 times stronger than soft tissue, than in this example the sum $h_{Ti}/1.3+h_{Di}$, should be kept constant in one row of the calibration object.

One example for an embodiment shown in FIG. 7 is a calibration object 1 built from a step wedge comprising a dark field active material, which is submerged into water, since water is a regular material and attenuates almost exactly like soft tissue.

With further reference to the embodiment shown in FIG. 7, a calibration object 1 can be built such that different rows—out of which one row is shown in side view in FIG. 7—correspond to different patient/sample/specimen heights.

The data acquired from exposing a calibration object according to any of the aforementioned embodiments of the invention, described with reference to FIG. 1 to FIG. 7, to X-ray beams can be used to linearize the performance of a dark field image and hence for calibration of the X-ray imaging system as regards dark field images. A method for calibration according to one embodiment of the invention is now described with reference to FIG. 8.

Figure 8:
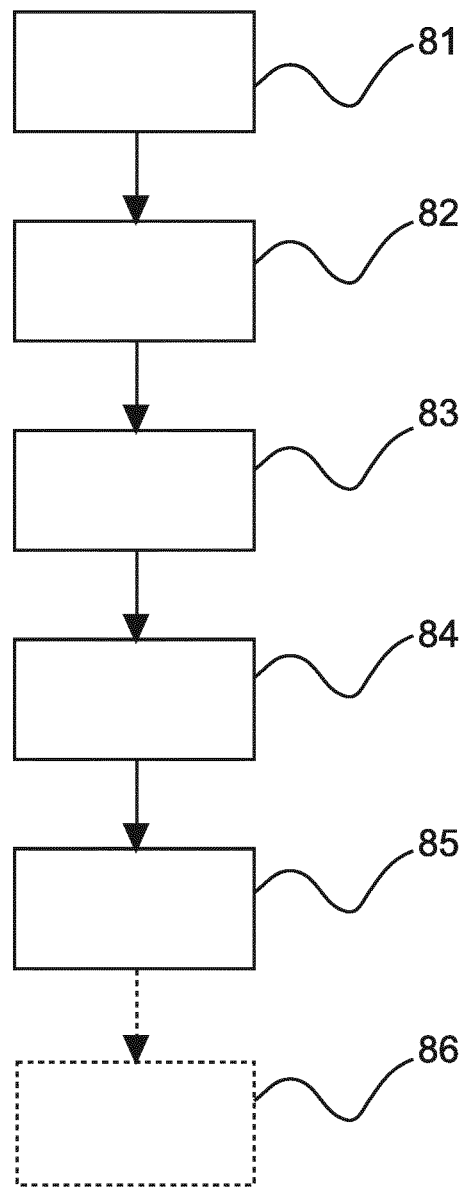
FIG. 8 schematically shows a flow-chart with method steps for calibrating an X-ray imaging device according to an exemplary embodiment of the present invention.

FIG. 8 schematically shows a flow-chart of method steps for a calibration according to one embodiment of the present invention. The following method steps are comprised: In step 81 a calibration object according to an embodiment of the invention is positioned in the beam path of an X-ray imaging device. Subsequently, in step 82, the calibration object is exposed to X-rays of the X-ray imaging device. In step 83, a dark field test image is acquired from the calibration object. For each section i of the calibration object pairs of values of $\log(T_i)$ and $\log(D_i)$ are obtained in step 84. $T_i$ denotes the normalized ratio of X-ray intensities and $D_i$ denotes the normalized ratio of visibilities corresponding to section i of the calibration object in the dark field test image of the calibration object.

The reasons for the determination of values $\log(T_i)$ and $\log(D_i)$ is as follows: as commonly known, X-ray beams are attenuated when passing through matter. In a good approximation, the attenuation follows an exponential law with attenuation coefficient $\mu$ as a parameter, the latter parameter being characteristic to the respective matter. The exponential behavior of the intensity can be written as $I=I_0 \cdot \exp[-\mu \cdot h]$ with h being the height of the object passed by the X-ray beam, $\mu$ the coefficient characterizing the matter composing the object, and $I_0$ the intensity of the non-attenuated X-ray in absence of the object. The negative log of $T=I/I_0$ is then proportional to the height h of the object. In experiments some deviation of this behavior can be observed due to beam hardening, which implies that $-\log(T)$ underestimates the true height h. The visibility V in dark field imaging behaves very similar. In good approximation it can be described as $V=V_0 \cdot \exp[-\varepsilon \cdot h \cdot C]$ with $\varepsilon$ denoting the diffusion coefficient , $V_0$ the visibility in absence of the object, and C a geometrical constant, see Bech et al., "Quantitative x-ray dark-field computed tomography", Phys. Med. Biol. 55 (2010) 5529-5539 (Eq. 20). For the sake of brevity, the constant C is assumed to be one here. The dark field signal is then defined as $D=V/V_0$. In the approximation mentioned above, the value $-\log(D)$ is the product of an object property, namely $\varepsilon$, and the height h of the object. It turns out, however, that the diffusion coefficient $\varepsilon$ also depends on the energy, thus different values of $\log(D)$ are measured if different amounts of attenuation material is in the beam. In a later diagnostic situation values of T and D—or equivalently $\log(T)$ and $\log(D)$—will be determined from an X-ray image of a patient/sample/specimen (for instance, a human thorax if the respective X-ray imaging system is used in lung imaging). These T and D values—or, equivalently, the corresponding $\log(T)$ and $\log(D)$ values—shall then be mapped to equivalent heights of regular material and dark field active material, respectively, in the patient/sample/specimen. During calibration of the X-ray imaging system, two functions shall therefore be established, $h_1(\log(T), \log(D))$ and $h_2(\log(T), \log(D))$. Thereby, the function $h_1$ gives the height of a regular material in dependence of measured values of $\log(T)$ and $\log(D)$. Similarly, the second function $h_2$ gives the height of a dark field active material as a function of measured values of $\log(T)$ and $\log(D)$. According to the above reasoning, the function $h_1$ is a more complicated function than just a linear function of $\log(T)$ only, which can be, amongst other effects, attributed to beam hardening effects. In a similar way, the function $h_2$ is a more complicated function than just a linear function of $\log(D)$. It should be noted that establishing during calibration the two functions $h_1$ and $h_2$ is equivalent to establishing during calibration a single function that maps (for each section of the calibration object) the measured values of $\log(T)$ and $\log(D)$ to a height of a regular material and to a height of a dark field active material.

Turning now to method step 85, the values of $\log(T_i)$ and $\log(D_i)$ are compared, for each section i, with expected values of design parameters of the calibration object. Thereby, design parameters can be the height—or, equivalently the thickness—of a subsection comprising the regular material and the height of a subsection comprising the dark field active material. From the comparison, a function mapping the values of $\log(T)$ and $\log(D)$ to the thickness of the respective subsections comprising the regular or dark field active material is constructed in method step 85. In this way, a linearization between the $\log(T)$ data and the height of regular material comprising subsections and a linearization between the $\log(D)$ data and the heights of the dark field active material comprising subsections is obtained. Optionally, in method step 86, a two-dimensional look-up table can be created from the comparison of the values $\log(T_i)$ and $\log(D_i)$ with expected design parameters, i.e. the heights or thicknesses of regular material or dark field active material comprising subsections, for each of the sections of the calibration object. In a further method step, the function, or, alternatively or additionally, the two-dimensional look-up table can be used to correct clinical images acquired as dark field images. Essentially, the calibration provides for a plurality of pairs of heights $h_{Ti}$ and $h_{Di}$ for the regular material and the dark field active material corresponding values of measurements $\log(T_i)$ and $\log(D_i)$. The indented use of these calibration data is to establish a general relationship for the inverse mapping, i.e., during the subsequent measurement of a patient or sample, some measurements of $\log(T)$ and $\log(D)$ are obtained and the corresponding equivalent heights $h_T$ and $h_D$ of the regular and dark field active material should be estimated. Since usually, the measured values of $\log(T_i)$ and $\log(D_i)$ do not span a regular grid, some so-called scattered data interpolation must be used in the calculation.

It should be noted, that the invention is not limited to conventional X-ray detectors, which are not energy resolving. Particularly, the invention also refers to the case of energy resolving X-ray detectors. In the latter case, for each resolvable X-ray energy, a value of $\log(T)$ and a value of $\log(D)$ might be taken for each section of the calibration object. For instance, two values of $\log(T)$ and $\log(D)$ might be taken for each section, such that a function can be constructed that maps between the four $\log(T)$ and $\log(D)$ values for each section and the heights of the regular and dark field active components in the respective section. This can lead to an even improved calibration. Having such an energy resolving detector, it is also advantageous to use a third material as it becomes possible to differentiate differently attenuation materials (such as soft-tissue and bones) in the beam.

As has been explained herebefore, the calibration object of the present invention facilitates that the dark field imaging system can be calibrated to achieve a better linear relation of object height and the logarithm of the dark field signal D. The more linear data will allow computer aided decision based on quantitative imaging.

The invention claimed is:

1. A calibration object for calibrating a dark field imaging device, the calibration object comprising:
   a plurality of sections,
      wherein a first section of the plurality of sections comprises a regular material and a dark field active material, the regular material primarily attenuating X-rays and the dark field active material primarily scattering the X-rays;
      wherein a second section of the plurality of sections comprises the regular material and the dark field active material,
      wherein a ratio of the regular material to the dark field active material is different in the first section than the second section, and
   a first step wedge and a second step wedge in each section,
      wherein the first step wedge comprises the regular material,
      wherein the second step wedge comprises the dark field active material, and
      wherein the first step wedge is combined with the second step wedge for calibration, and a plurality of data points acquired from exposing the plurality of sections to the X-rays are linearized in order to calibrate the dark field imaging system.

2. The calibration object according to claim 1, wherein the regular material comprises one of the materials comprising PMMA (Polymethylmethacrylat), POM (Polyoxymethylen), PE (Polyethylen), Aluminum, or any combination thereof.

3. The calibration object according to claim 1, wherein the dark field active material comprises one of the materials comprising tissue, glass spheres, glass spheres in resin, foam, glass fibers, or any combination thereof.

4. The calibration object according to claim 1,
   wherein the first and second sections comprise an additional material which is the regular material or the dark field active material.

5. The calibration object according to claim 1,
   wherein the first section comprises a first subsection with a first height and a second subsection with a second height,
   wherein the first and the second subsection of the first section do not overlap,
   wherein the second section comprises a first subsection with a first height and a second subsection with a second height,
   wherein the first and the second subsections of the second section do not overlap,
   wherein the first height of the first subsection of the first section differs from the first height of the first subsection of the second section,
   wherein the second height of the second subsection of the first section differs from the second height of the second subsection of the second section,
   wherein the regular material contained in the first section is contained in the first subsection of the first section and the dark field active material contained in the first section is contained in the second subsection of the first section, and
   wherein the regular material contained in the second section is contained in the first subsection of the second section and the dark field active material contained in the second section is contained in the second subsection of the second section.

6. The calibration object according to claim 1,
   wherein each of the first and the second step wedges has at least 3 steps,
   wherein the second step wedge is arranged after the first step wedge along a predetermined axis, and
   wherein the second step wedge is arranged over the first step wedge and is 90° rotated in a plane rectangular to the predetermined axis with respect to orientation of the first step wedge.

7. The calibration object according to claim 1, further comprising an other step wedge comprising the dark field active material,
   wherein the other step wedge is submerged into a fluid,
   wherein the fluid comprises the regular material.

8. The calibration object according to claim 1, wherein the first and second sections have substantially equal height.

9. A method for calibrating a dark field imaging device using a calibration object, the method comprising:
   providing a plurality of sections, wherein a first section of the plurality of sections comprises a regular material and a dark field active material, the regular material primarily attenuating X-rays and the dark field active material primarily scattering the X-rays; wherein a second section of the plurality of sections comprises the regular material and the dark field active material; wherein a ratio of the regular material to the dark field active material is different in the first section than the second section; wherein each section comprises a first step wedge and a second step wedge; wherein the first step wedge comprises the regular material; wherein the second step wedge comprises the dark field active material;

combining the first step wedge with the second step wedge;

positioning the calibration object in a beam path of the X-ray imaging device;

exposing the calibration object to the X-rays of the X-ray imaging device;

acquiring a plurality of data points in a dark field test image from the calibration object; and linearizing the plurality of data points in order to calibrate the dark field imaging device.

10. The method according to claim 9, wherein for each section of the calibration object at least two pairs of values are obtained corresponding to different X-ray energies.

11. The method according to claim 10, further comprising generating a two-dimensional look-up table from a comparison of the values for each section of the calibration object with heights of the regular and the dark field active material.

12. A non-transitory computer-readable medium having one or more executable instructions stored thereon, which when executed by a processor, cause the processor to perform a method for calibrating a dark field imaging device using a calibration object, the method comprising:

providing a plurality of sections, wherein a first section of the plurality of sections comprises a regular material and a dark field active material, the regular material primarily attenuating X-rays and the dark field active material primarily scattering the X-rays; wherein a second section of the plurality of sections comprises the regular material and the dark field active material; wherein a ratio of the regular material to the dark field active material is different in the first section than the second section; wherein each section comprises a first step wedge and a second step wedge; wherein the first step wedge comprises the regular material; wherein the second step wedge comprises the dark field active material;

combining the first step wedge with the second step wedge;

positioning the calibration object in a beam path of the X-ray imaging device;

exposing the calibration object to the X-rays of the X-ray imaging device;

acquiring a plurality of data points in a dark field test image from the calibration object; and linearizing the plurality of data points in order to calibrate the dark field imaging device.

* * * * *